United States Patent
Bartholomeusz

(10) Patent No.: US 10,894,074 B2
(45) Date of Patent: Jan. 19, 2021

(54) MULTI-FACTOR HAIR GROWTH FORMULATION

(71) Applicant: SKINQRI, LLC, Lincolnshire, IL (US)

(72) Inventor: James Bartholomeusz, Beverly Hills, CA (US)

(73) Assignee: SKINQRI, LLC, Lincolnshire, IL (US)

(*) Notice: Subject to any disclaimer, the term of this patent is extended or adjusted under 35 U.S.C. 154(b) by 61 days.

(21) Appl. No.: 16/178,693

(22) Filed: Nov. 2, 2018

(65) Prior Publication Data

US 2019/0134142 A1 May 9, 2019

Related U.S. Application Data

(60) Provisional application No. 62/581,103, filed on Nov. 3, 2017.

(51) Int. Cl.

| | | |
|---|---|---|
| *A61K 38/02* | (2006.01) | |
| *A61P 17/04* | (2006.01) | |
| *A61K 38/18* | (2006.01) | |
| *A61K 8/64* | (2006.01) | |
| *A61K 38/30* | (2006.01) | |
| *A61K 35/16* | (2015.01) | |
| *A61K 38/27* | (2006.01) | |
| *A61K 38/22* | (2006.01) | |
| *A61Q 7/00* | (2006.01) | |
| *A61P 17/00* | (2006.01) | |
| *A61K 9/00* | (2006.01) | |
| *A61K 9/127* | (2006.01) | |
| *A61K 9/51* | (2006.01) | |

(52) U.S. Cl.
CPC ............ *A61K 38/02* (2013.01); *A61K 8/64* (2013.01); *A61K 9/0014* (2013.01); *A61K 9/127* (2013.01); *A61K 9/51* (2013.01); *A61K 35/16* (2013.01); *A61K 38/18* (2013.01); *A61K 38/1808* (2013.01); *A61K 38/1825* (2013.01); *A61K 38/1866* (2013.01); *A61K 38/2278* (2013.01); *A61K 38/2292* (2013.01); *A61K 38/27* (2013.01); *A61K 38/30* (2013.01); *A61P 17/00* (2018.01); *A61P 17/04* (2018.01); *A61Q 7/00* (2013.01)

(58) Field of Classification Search
None
See application file for complete search history.

(56) References Cited

U.S. PATENT DOCUMENTS

| | | |
|---|---|---|
| 7,095,569 B2 | 8/2006 | Rege et al. |
| 7,241,731 B2 | 7/2007 | Hirai et al. |
| 7,404,498 B2 | 7/2008 | Hattori et al. |
| 7,560,428 B2 | 7/2009 | Hirai et al. |
| 7,750,115 B2 | 7/2010 | Oka et al. |
| 2011/0081802 A1 | 4/2011 | Knepp |
| 2012/0021029 A1 | 1/2012 | Sanz et al. |
| 2012/0039837 A1 | 2/2012 | Somfleth et al. |
| 2012/0054034 A1 | 3/2012 | Mattingly et al. |
| 2012/0065131 A1 | 3/2012 | Dake et al. |
| 2013/0011356 A1 | 1/2013 | Fahnestock et al. |
| 2014/0069452 A1 | 3/2014 | Krueger |
| 2015/0265516 A1 | 9/2015 | Anzali et al. |
| 2015/0272860 A1 | 10/2015 | Mette et al. |
| 2016/0199282 A1 | 7/2016 | Wiesche et al. |
| 2016/0199498 A1 | 7/2016 | Dai et al. |

OTHER PUBLICATIONS

Anonymous "Truly Natural and Safe Ingredients to Human Skin from Regeron" Cosmetics Business https://www.cosmeticsbusiness.com/news/article_page/Truly_Natural_and_Safe_Ingredients_to_Human_Skin_from_Regeron/92492 (Year: 2013).*

* cited by examiner

*Primary Examiner* — Larry D Riggs, II
*Assistant Examiner* — Zachary J Miknis
(74) *Attorney, Agent, or Firm* — McDonald Hopkins LLC

(57) ABSTRACT

A synergistic, multi-factor hair growth formulation and its method of use are described. A plurality of synthetic peptides and proteins are selected to maximize efficacy at discrete stages of the anagenic growth phase of a hair follicle, and these compounds may be further coated to promote uptake into the skin and/or hair root. The formulation itself is topical, so as to allow for direct, selective application alone or in combination with mechanical or energetic delivery techniques.

13 Claims, 1 Drawing Sheet

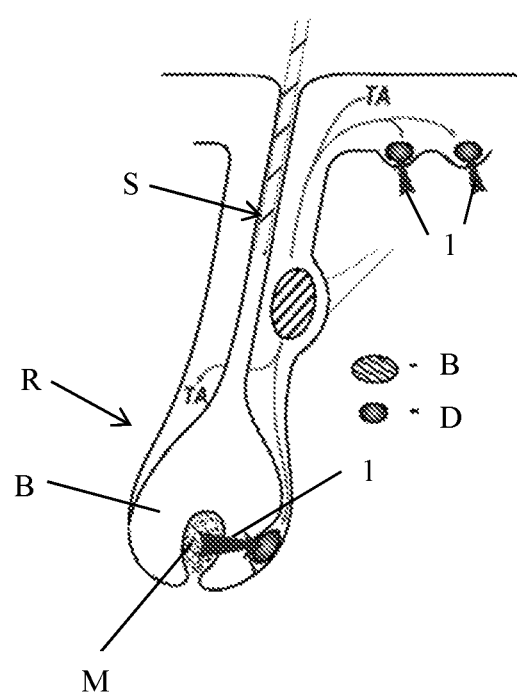

MULTI-FACTOR HAIR GROWTH FORMULATION

CROSS-REFERENCE TO RELATED APPLICATION

This application claims priority to U.S. Provisional Patent Application No. 62/581,103 entitled "MULTI-FACTOR HAIR GROWTH FORMULATION," filed on Nov. 3, 2017, which is incorporated herein by reference in its entirety.

TECHNICAL FIELD

The present invention relates generally to a method and formulation for promoting hair growth and, more particularly, to a synergistic blend of oligiopeptides and growth factors selected to address differing stages of the human hair growth cycle, as well as methods of using such blends to promote hair growth.

BACKGROUND

Hair loss prevention has been a topic of considerable interest. Numerous methods and compounds have been suggested to prevent loss of hair and/or to promote the growth of new hair. These approaches include medications such as finasteride (sold under the brand name Propecia) and minoxidil (sold as Rogaine), as well as individual oligopeptides or growth factors which, on an individual basis, are alleged to prevent hair loss and/or promote hair regeneration and growth.

U.S. Pat. Nos. 7,750,115; 7,560,428; 7,404,498; 7,241,731; and 7,095,569 disclose a variety of peptides, peptidic conjugates, and growth factor proteins that are individually alleged to promote hair growth and/or treat hair loss conditions such as alopecia. In the same manner, a number of pending patent publications describe peptides and other compositions in this regard, such as United States Patent Publication 2016/0199498; 2016/0199282; 2015/0272860; 2015/0265516; 2014/0069452; 2013/0011356; 2012/0065131; 2012/0054034; 2012/0039837; 2012/0021029; and 2011/081802. Additional methods and other delivery systems are also described.

In each instance, the methods, the prescriptions, and/or oligopeptides appear to approach the question as a simple, single mechanism. In some instances, the efficacy of these documents is implicitly or explicitly premised on the discovery that a single compound or method is more effective than previously known approaches.

SUMMARY

The current invention improves over previously disclosed formulations by considering the context of the hair growth cycle. In this manner, the inventors were able to utilize a combination of different items which provides an overall synergistic effect that vastly improves the efficacy of the hair growth treatment, particularly when coupled with specific means of introducing the serum containing that formulation to the scalp.

By considering the question from the perspective of hair damage mechanisms, a multi-factored composition was identified to treat the anagenic phase, the progenitor cells associated with hair follicle, and stimulation of hair of the hair bulge. Additionally, compounds and methods which assist and improve upon underlying blood circulation within the scalp can be included to further enhance the efficacy of the final composition, including mechanical or energetic means.

One aspect of the invention contemplates a method for promoting hair growth. It includes any combination of the following features:
  creating a formulation from a plurality of synthetic peptides and growth factors associated with anagenic phase hair growth, including at least one selected from group 2 and at least one selected from group 3, selected from:
    in group 1: follistatin (Wnt 7a), acidic fibroblast growth factor (aFGF), basic fibroblast growth factor (bFGF);
    in group 2: protein rich plasma (PRP), human growth hormone (Hgh), vasoactive endothelial growth factor (VEFG), insulin-like growth factor (IGF);
    in group 3: epidermal growth factor (EGF), keratin growth factor (KGF), vasoactive intestinal polypeptide (VIP); and
    in group 4: thymosin beta 4;
  topically applying the formulation to a skin surface of a subject, wherein the topically applying promotes uptake of the formulation into the skin surface but without ingestion or uptake of the formulation into the subject's bloodstream;
  wherein at least Hgh is selected from group 2 and at least VIP and EGF are selected from group 3;
  wherein the topically applying the formulation includes at least one of mechanical delivery means and energetic delivery means;
  wherein the mechanical delivery means are selected from diliation of pores in the skin surface through use of a diliating or vaso-diliating agent, applying positive pressure to pores in the skin surface, applying negative pressure to pores in the skin surface, and puncturing the skin surface with one or more needles;
  wherein the energetic delivery means are selected from iontophoresis, applying ultrasonic energy to the skin surface, applying visible light to the skin surface, applying radio waves to the skin surface, and creating temporary, fractional injuries in the skin surface with laser light;
  wherein at least one of the synthetic peptides is individually encapsulated within at least one of lipids and nanoliposomes to create encapsulated particles;
  wherein the topically applying the formulation includes creating temporary, fractional injuries in the skin surface, said injuries having a width which accommodates the encapsulated particles;
  wherein the width of the injuries is between 100 and 500 microns and wherein a depth of the injury is proximate to and no greater than a level of hair roots beneath the skin surface;
  wherein the formulation also contains at least one selected from group 4; and
  wherein the formulation also contains at least one selected from group 1

In another aspect, a topical mixture of active ingredients for promoting all stages during an anagenic phase of human growth is described. The mixture includes sh-oligopeptide-1, sh-polypeptide-7, and sh-polypeptide-71.

In a separate aspect, the topical mixture may consist essentially of any combination of the following features:
  a combination of synthetic peptides including sh-oligopeptide-1, sh-oligopeptide-4, sh-polypeptide-7, sh-polypeptide-11, and sh-polypeptide-71;
  inactive components including an encapsulating material;
  wherein the encapsulating material is a nanoliposome;

wherein at least one of the synthetic peptides is individually encapsulated as particles having a size between 100 and 500 microns;

wherein the combination of synthetic peptides also includes sh-polypeptide-2 and sh-polypeptide-9 and wherein an amount of sh-polypeptide-71 in the combination of synthetic peptides is comparatively lowest and an amount of sh-oligopeptide-1 in the combination of synthetic peptides is comparatively greatest;

wherein the combination of synthetic peptides also includes sh-polypeptide-1 and sh-polypeptide-9 and wherein an amount of sh-oligopeptide-1 in the combination of synthetic peptides is comparatively lowest and an amount of sh-polypeptide-71 in the combination of synthetic peptides is comparatively greatest;

wherein, in the combination of synthetic peptides, sh-polypeptide-7, sh-oligopeptide-4, sh-polypeptide-1, sh-polypeptide-9, and sh-polypeptide-11 are provided in an approximately equal amounts that are between the amount of sh-oligopeptide-1 and the amount sh-polypeptide-71;

wherein the combination of synthetic peptides also includes sh-polypeptide-1;

wherein the inactive components include at least one solvent, a surfactant, an antioxidant, a masking agent, and a smoothing agent;

wherein the solvents are pentylene glycol and water, the surfactant is polysorbate, the antioxidant is ascorbyl glucoside, the chelator is disodium ethylenediaminetetaacetic acid, the smoothing agent is niacinamide; and wherein the inactive components consist essentially of pentylene glycol, water, polysorbate, ascorbyl glucoside, disodium ethylenediaminetetraacetic acid, niancinamide, panethenol, and arginine.

A method of preparing at least some of the aforementioned aspects of topical mixtures is also contemplated. This method may include any combination of the following:

mixing the inactive components into a solvent to create a solution;

heating the solution to 50° C.;

allowing the solution to cool to less than 40° C. and then mixing the combination of synthetic peptides into the solution; and wherein the combination of synthetic peptides are mixed into the solution when the solution is at approximately 35° C.

Methods for promoting hair growth are also contemplated in some aspects of the invention. Here, these methods may include any combination of the following:

creating any topical mixture encompassed by the disclosure of paragraph 9 above;

applying the topical mixture to a skin surface of a subject, wherein the topically applying promotes uptake of the formulation into the skin surface but without ingestion or uptake of the formulation into the subject's bloodstream;

wherein the applying the mixture includes at least one of mechanical delivery means and energetic delivery means;

wherein the mechanical delivery means are selected from diliation of pores in the skin surface through use of a diliating or vaso-diliating agent, applying positive pressure to pores in the skin surface, applying negative pressure to pores in the skin surface, and puncturing the skin surface with one or more needles;

wherein the energetic delivery means are selected from iontophoresis, applying ultrasonic energy to the skin surface, applying visible light to the skin surface, applying radio waves to the skin surface, and creating temporary, fractional injuries in the skin surface with laser light;

prior to applying the mixture, individually encapsulating at least one of the synthetic peptides within at least one of lipids and nanoliposomes to create encapsulated particles;

wherein the applying the mixture includes creating temporary, fractional injuries in the skin surface, said injuries having a width which accommodates the encapsulated particles; and wherein the width of the injuries is between 100 and 500 microns and wherein a depth of the injury is proximate to and no greater than a level of hair roots beneath the skin surface.

Specific reference is made to the appended claims, drawings, and description below, all of which disclose elements of the invention. While specific embodiments are identified, it will be understood that elements from one described aspect may be combined with those from a separately identified aspect. In the same manner, a person of ordinary skill will have the requisite understanding of common processes, components, and methods, and this description is intended to encompass and disclose such common aspects even if they are not expressly identified herein.

DESCRIPTION OF THE DRAWINGS

Operation of the invention may be better understood by reference to the detailed description taken in connection with the following illustrations. These appended drawings form part of this specification, and any written information in the drawings should be treated as part of this disclosure. In the same manner, the relative positioning and relationship of the components as shown in these drawings, as well as their function, shape, dimensions, and appearance, may all further inform certain aspects of the invention as if fully rewritten herein.

In the drawings:

FIG. 1 is a cross sectional side view illustration of a human hair follicle. Hair shaft S extends into the subject's skin connecting to hair root R. Root R comprises hair bulb B and hair matrix/papilla M. Bulge located stem cells B, derivative stem cell populations D, and transient amplifying cells TA are located proximate to these structures, while arrows 1 indicate the modifying influence of adjacent mesenchyme.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. As such, the following description is presented by way of illustration only and should not limit in any way the various alternatives and modifications that may be made to the illustrated embodiments and still be within the spirit and scope of the invention.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

Both protein rich plasma (PRP) and human adipose-derived stem cell media contain some of the growth factors inherent to the prior art methods and compounds mentioned above. However, the inventors have discovered, since specific growth factors are more important than others in relation to hair growth, using only a single type growth factor and/or a fixed concentration of the mix of factors found in PRP and/or adipose-derived factors is not desirable.

The inventive method focuses on a holistic range of growth factors specifically selected for aspects of hair growth, as well as a number of means to promote uptake of serums containing such formulations. As such, the invention is distrinct from disclosures that coincidentally identify a single growth factor (e.g., as pertinent in the context of wound healing or other uses not immediately associated with hair growth) and/or a method of promoting uptake that is not necessarily associated with the aims of this invention.

First, the inventors considered the entirety of the hair growth cycle. Generally speaking, a hair follicle—generally illustrated in FIG. 1—has a three phase life cycle. The anagen phase refers to actual growth, with the root dividing and adding structure and length to the hair shaft itself. The catagen phase is a transitional period from growth to rest, with blood supply being cut off from the cells that normally produce new hair. The final phase, the telogen phase, results in dead hair that may be lost/shed from the scalp.

Rather than focus on the broad anagen phase (which can last several years), the inventors identified four additional stages of that phase: 1) hair follicle induction; 2) hair follicle formation via stem cell proliferation; 3) growth of the hair shaft itself; and 4) microcirculation. By considering these additional stages—rather than generically referring to overall hair growth in the anagen phase—the inventors were able to identify and optimize specific growth factors and synthetic peptides that improve and influence hair growth. Notably, each hair will independently follow this cycle, such that a substantial portion of the individual hairs will be actively growing in a variety of these phases at any given time. Thus, by providing formulations that address all of the phases, rather than focusing on a single component to influence a single phase or stage, the inventive hair growth methods and formulations achieve improved results in comparison to prior art solutions wherein only a single growth factor or a single stage the hair growth phase is contemplated.

Additionally, instead of approaching the question of hair loss as one to be treated by orally ingested medication, the inventors deliberately selected an approach that considered topical application. In this manner, the treatment can be more selectively applied, either as a spray or serum. As used herein, it will be understood that topical application means the spray or serum (or whatever form the mixtures of compounds described herein may take) is applied to the surface of the skin without entering the bloodstream or otherwise being ingested by other organs or tissue.

In particular, physical application may be by way of direct physical contact. This contact can include deliberate, fractional injuries and/or physical manipulation/movement of the skin and pores to facilitate penetration of the formulation down to hair root itself. These manipulations or injuries can be characterized as mechanical or energetic in nature. While each will be discussed separately below, it may be possible to incorporate a combination of these techniques to further improve the uptake of the formulation and, ultimately, the efficacy of the treatment/application.

With respect to mechanical methods, these can be subdivided into diliation, pressure, and puncture methods. Diliation may include vasodilating compounds or negative pressure vacuums which effectively open pores and/or create voids in the skin so as to allow the formulation to come into closer proximity with the hair root. In contrast, pressure methods include the application of positive pressure so as to force the formulation into and through the skin, with vibration and massage of exposed skin being examples. Puncture methods contemplate the use of small needles (e.g., 32 gauge needles create 300 micron openings) or puncturing apparatus that to create a plurality of temporary openings.

Energetic methods may rely on electrical current, sonic energy, and/or electromagnetic radiation. In particular, galvanic current (e.g., iontophoresis) can be applied to the skin open pores. Ultrasonic energy, lasers, visible light (e.g., red light), or radio waves (or other non-visible light) are also possibilities. Notably, some of these additional possibilities create openings in the top layer of the skin by way of fractional injury, while others create a temporary physiological response and/or mimic vibration and direct positive pressure (similar to the mechanical methods noted above) to accomplish the same effects. In each instance, these energetic means may be used in combination with positive pressure to work the formulation into the skin.

Preferably, the openings or voids created by any of the delivery methods above should be between about 100 to 500 microns wide so as to accommodate the nanolipsome encapsulated particles described below. It may be possible to rely on even larger openings (e.g., less than 1000 microns, less than 750 microns, less than 600 microns, less than 500 microns, etc.), although consideration should be given to the comfort of the patient. The minimum size of the openings can be dictate by the size of the encapsulated particle (e.g., at least 100 microns, at least 200 microns, at least 250 microns, at least 300 microns, etc.). The depth of the openings does not need to penetrate the epidermis and, instead, should be calibrated to be in proximity with the hair roots. Notably, there is no need to have the formulation enter the bloodstream, such that the delivery methods are effectively intra-dermal and do not cause permanent injury or result in significant bleeding.

The components of the formulation can be individually encapsulated and then mixed as part of the formulation processes contemplated below, although it may also be possible to create the entire formulation and then encapsulate that mixture. Additionally or alternatively, only selected components could be encapsulated. For example, the active ingredients (e.g., the synthetic peptides and growth factors identified below) need to be encapsulated, while the inactive components could be provided in solution, serum, powder, slurry/suspension, or some other form.

With respect to the formulation itself, a plurality of synthetic peptides and growth factors were associated with each of the four anagenic stages identified above. In stage 1, follistatin (Wnt 7a) and/or acidic fibroblast growth factor (aFGF), basic fibroblast growth factor (bFGF) were identified as useful in facilitating the switch from catagen/telogenic phases back to the anagenic phase, as well as potentially helpful in promoting the induction of new follicular bulbs.

In order to increase growth factors around the now-induced follicle unit in stage 2, up to four separate growth factors could be significant. These factors relate to wound healing and may include PRP, as well as human growth hormone (Hgh) and vascular or vasoactive endothelial growth factor (VEFG). Additionally, insulin-like growth factor (IGF) could be useful in this stage.

Growth of the hair shaft itself in stage 3 may determine the density, length, and color of the resulting hair. Further, certain skin proteins may be expressed at this stage. As such, key active compounds include epidermal growth factor (EGF), keratin growth factor (KGF), and/or vasoactive intestinal polypeptide (VIP) are significant, particularly in connection with the bulge cells during the anagen phase.

Finally, in stage 4, a combination of growth factors, skin proteins, and manual/mechanical massage prove to be useful. In particular, neo-vascularization and/or angiogenesis is desired at or around the follicle during this stage. The active compound most useful for these purposes is thymosin beta 4.

As noted above, the use mechanical and/or energetic delivery methods, as well as massage/physical contact, may prove useful to enhance topical penetration and maintain healthy scalp circulation. Further, these compounds—and particularly some or all of the active ingredients—may be individually or collectively coated or encapsulated in biocompatible coatings to further facilitate delivery. The encapsulation reduces the formulation to an optimal, consistent size (relative to the "particle" formed by the encapsulation material) that is compatible with the selected delivery method. For example, with respect to mechanical methods such as micro-puncturing, the formulation (or some or all of the individual components of the formulation) is coated and encapsulated with an appropriately biocompatible material so as to impart a particle size that is less than the needle size (e.g., particle size of 200 microns with 32-gauge needles having an outer diameter of approximately 300 microns), thereby allowing the encapsulated formulation to penetrate the top layer of skin and, ultimately, come into closer proximity to the hair root itself.

In terms of formulations that sufficiently accommodate the various phases and stages as described above, the inventors combined a series of peptides and growth factors that were previously only considered useful on an individual basis. Thus, table 1 below describes one embodiment of the invention. The composition incorporates a plurality of different oligopeptides and polypeptides. The formulation may also include a number of inactive components, including water, glycerol, lecithin, polysorbate 60, sodium citrate, citric acid, and/or phenoxyethanol.

TABLE 1

Basic hair growth promotion formulation.

| Peptide of interest | Physical properties |
| --- | --- |
| rh-oligopeptide-β4 | pH = 7; mol. wt. 5.05 kDa |
| oligopeptide-71 | pH = 7; mol. wt. 1447.6 kDa |
| sh-oligopeptide-1 | pH = 6; single chain polypeptide produced by E. Coli; no protease activity; encapsulated in a liposome-based carrier (trade name Clairesome); "low" molecular weight (but no stated basis/measurement) with 53 amino acids; characterized as equivalent to epidermal growth factor (EGF) |
| sh-oligopeptide-11 | pH = 6 |
| sh-polypeptide-1 | pH = 6 |
| sh-polypeptide-7 | pH = 6; single chain polypeptide produced by E. Coli; mol. wt. 24.1 kDa with 192 amino acids; characterized as equivalent to human growth hormone (Hgh) and/or somatotropin; comparable to minoxidil for hair growth treatment |
| sh-polypeptide-71 | pH = 6; encapsulated in a liposome-based carrier; produced by chemical peptide synthesis with 28 amino acids; characterized as equivalent to vasoactive intestinal polypeptide (VIP) |

A second embodiment is provided in Table 2. This formulation should remain refrigerated, preferably between 2° and 8° C.

TABLE 2

Basic hair growth promotion formulation.

| International Nomenclature of Cosmetic Ingredients | w/w % |
| --- | --- |
| sh-Oligopeptide-1 | 0.00186 to 0.00386 |
| sh-Polypeptide-7 | 0.00043 to 0.00243 |
| sh-Polypeptide-9 | 0.00043 to 0.00243 |
| sh-Oligopeptide-4 | 0.00043 to 0.00243 |
| sh-Polypeptide-11 | 0.00023 to 0.00063 |
| sh-Polypeptide-2 | 0.00023 to 0.00063 |
| sh-Polypeptide-71 | 0.00004 to 0.00024 |
| Inactives | 2.77000 to 4.77000 |
| Water | Add to make 100 units |

The inactives may include glycerin (@ 2.0 w/w %), lecithin (@ 1.0 w/w %), Polysorbate 60 (@ 0.300 w/w %), sodium citrate (@ 0.150 w/w %), and citric acid (@ 0.020 w/w %). However, other inactives may be used, so long as the substituted, added, or omitted substances fulfill substantially similar roles as the disclosed blend. Also, the mass percentages in Table 2 are relative, so as to allow for easy scaling. Notably, any value within the range is contemplated, and three equally spaced intervals (in addition to the upper and lower limits) are specifically disclosed herein for each item (e.g., if the range disclosed is 0.00 to 1.00, this disclosure expressly includes at least 0.00, 0.25, 0.50, 0.750, and 1.00).

A third embodiment is provided in Table 3a. When preparing this composition, homogenization should be employed by slow addition and mild mixing of the compounds to avoid foaming. Alcohols should be minimized, as they may negatively impact the stability of certain active ingredients. Less than 10 w/w % of ethanol is preferred. Here again, in addition to the specifically disclosed lower and upper values, this table expressly discloses three equally spaced intervals in addition to these upper and lower limits for each line item.

TABLE 3a

Basic hair growth promotion formulation.

| Compound, International Nomenclature of Cosmetic Ingredients | Purpose | Sequence | w/w % |
| --- | --- | --- | --- |
| Pentylene glycol | Solvent | A | 0.000 to 7.000 |
| Polysorbate 60 | Surfactant | A | 0.000 to 0.200 |
| Ascorbyl glucoside | Antioxidant | B | 0.000 to 0.100 |
| Disodium ethylenediaminetetraacetic | Chelator | B | 0.000 to 0.040 |

TABLE 3a-continued

Basic hair growth promotion formulation.

| Compound, International Nomenclature of Cosmetic Ingredients | Purpose | Sequence | w/w % |
|---|---|---|---|
| acid (EDTA), >99% purity | | | |
| p-anisic acid | Masking agent | B | 0.000 to 0.200 |
| Niacinamide | Smoothing agent | B | 0.000 to 1.000 |
| Panthenol | Hair conditioning | A | 0.000 to 1.000 |
| Arginine, >98% purity | Hair conditioning | B | 0.000 to 0.400 |
| Sh-polypeptide-7* | Hair conditioning | C | 1.000 to 5.000 |
| Sh-polypeptide-11* | Hair conditioning | C | 1.000 to 5.000 |
| Sh-polypeptide-1* | Hair conditioning | C | 1.000 to 5.000 |
| Sh-oligopeptide-1* | Hair conditioning | C | 1.000 to 5.000 |
| Sh-polypeptide-71* | Hair conditioning | C | 1.000 to 7.000 |
| Sh-Oligopeptide-4 | Hair conditioning | C | 1.000 to 5.000 |
| Sh-Oligopeptide-1 | Hair conditioning | C | 0.500 to 2.500 |
| Water | Solvent | A | Add to make 100 units |

*These compounds are provided at ~0.5 to 2 ppm with water, lecithin, sodium phosphate, pheoxyethanol, and disodium EDTA. The active protein should be at least 95% pure.

In certain embodiments, it may be possible to employ a specific sequence of heating and mixing to further improve the efficacy. The compounds associated with sequence group A are slowly mixed and heated to 50° C. Group B compounds are then added, again with good mixing. The resulting mixture is allowed to cool to at least 40° C. (and more preferably less than 35° C.), at which point group C is added with good mixing. A cross linked polyacrylic acid polymer may also be employed. Water used herein should preferably be distilled and/or deionized.

Table 3b discloses yet another formulation that is appropriate for mixing at room temperature. Each of the hair conditioning components should be added slowly and under sufficiently controlled mixing so as to avoid the formation of foam. Each may be pre-mixed with comparable amounts of water, glycerin, lechtin, polysorbate 60, sodium citrate, citric acid, and/or phenoxyethanol (for the purposes identified above). Any value within the range is contemplated, and three equally spaced intervals (in addition to the upper and lower limits) are specifically disclosed herein for each item.

TABLE 3b

Basic hair growth formulation

| International Nomenclature of Cosmetic Ingredients | w/w % |
|---|---|
| sh-Polypeptide-7 | 12.340 to 16.340 |
| sh-Polypeptide-11 | 12.340 to 16.340 |
| sh-Polypeptide-1 | 12.340 to 16.340 |
| sh-Oligopeptide-1 | 6.200 to 8.200 |
| sh-Polypeptide-71 | 19.100 to 23.100 |
| sh-Polypeptide-9 | 12.340 to 16.340 |
| sh-Oligopeptide-4 | 12.340 to 16.340 |

Thus, additional formulations based on the four stage approach described above are possible. In the most abstract form, the invention may encompass selecting the proteins, peptides, and/or growth factors (or their functional equivalents) to address each of the stages identified by the inventors. In this manner, a synergistic and heretofore unrealized level of efficacy can be attained in the promotion of hair growth. Further, given the topical application, it is possible to selectively apply the formulation to the areas desired to experience hair growth. In this manner, some of the shortcomings of oral medications or broad-based treatments can be diminished.

Any of the embodiments contemplated above can be encapsulated. The encapsulating material(s) should be biocompatible material and capable of eventually releasing the encapsulated material. Lipids, liposomes, and proteins, and particularly nanoliposomes, are useful in this regard. Non-limiting example of such encapsulating materials can be found in U.S. Pat. Nos. 7,951,396 and 8,846,611, which are both incorporated by reference herein. Preferably, the active components are individually encapsulated and then mix them at the desired proportions noted above, although it may be possible to encapsulate the final formulation in its entirety.

Although the present embodiments have been illustrated in the accompanying drawings and described in the foregoing detailed description, it is to be understood that the invention is not to be limited to just the embodiments disclosed, and numerous rearrangements, modifications and substitutions are also contemplated. The exemplary embodiment has been described with reference to the preferred embodiments, but further modifications and alterations encompass the preceding detailed description. These modifications and alterations also fall within the scope of the appended claims or the equivalents thereof.

Understanding that the formulations herein necessarily include multiple components and that each component is indicated as having a range of possible concentration values, contemplated embodiments encompass any combination of selected values for each disclosed range (e.g., if component A is provided at 0.1% to 0.5%; component B at 1.0% to 2.0%; and component C at 0.2% to 0.6%, then non-limiting exemplary embodiments may include at least three separate formulations where, in a first example, component A is 0.1%, component B is 2.0%, and component C is 0.2%, while in a second example is component A at 0.1%, component B at 1.0%, and component C at 0.2% and a third example is component A at 0.5%, component B at 1.0%, and component C at 0.6%, etc.).

What is claimed is:

1. A topical mixture of active ingredients for promoting all stages during an anagenic phase of human hair growth, the mixture comprising:
    a combination of synthetic peptides including sh-oligopeptide-1, sh-oligopeptide-4, sh-polypeptide-7, sh-polypeptide-11, and sh-polypeptide-71; and
    inactive components.

2. The topical mixture according to claim 1 wherein the inactive components include an encapsulating material.

3. The topical mixture according to claim 2 wherein the encapsulating material is a nanoliposome.

4. The topical mixture according to claim 3 wherein at least one of the synthetic peptides is individually encapsulated as particles having a size between 100 and 500 microns.

5. The topical mixture according to claim 1 wherein the combination of synthetic peptides also includes sh-polypeptide-2 and sh-polypeptide-9 and wherein an amount of sh-polypeptide-71 in the combination of synthetic peptides is lowest and an amount of sh-oligopeptide-1 in the combination of synthetic peptides is greatest.

6. The topical mixture according to claim 1 wherein the combination of synthetic peptides also includes sh-polypeptide-1 and sh-polypeptide-9 and wherein an amount of sh-oligopeptide-1 in the combination of synthetic peptides is lowest and an amount of sh-polypeptide-71 in the combination of synthetic peptides is greatest.

7. The topical mixture according to claim 6 wherein, in the combination of synthetic peptides, sh-polypeptide-7, sh-oligopeptide-4, sh-polypeptide-1, sh-polypeptide-9, and sh-polypeptide-11 are provided in an approximately equal amounts that are between the amount of sh-oligopeptide-1 and the amount sh-polypeptide-71.

8. The topical mixture according to claim 1 wherein the combination of synthetic peptides also includes sh-polypeptide-1.

9. The topical mixture according to claim 8 wherein the inactive components include at least one solvent, a surfactant, an antioxidant, a masking agent, and a smoothing agent.

10. The topical mixture according to claim 9 wherein the solvents are pentylene glycol and water, the surfactant is polysorbate, the antioxidant is ascorbyl glucoside, the chelator is disodium ethylenediaminetetaacetic acid, the smoothing agent is niacinamide.

11. The topical mixture according to claim 8 wherein the inactive components consist essentially of pentylene glycol, water, polysorbate, ascorbyl glucoside, disodium ethylenediaminetetraacetic acid, niancinamide, panethenol, and arginine.

12. A method of preparing the topical mixture of claim 9 comprising:
   mixing the inactive components into a solvent to create a solution;
   heating the solution to 50° C.; and
   allowing the solution to cool to less than 40° C. and then mixing the combination of synthetic peptides into the solution.

13. The method according to claim 10 wherein the combination of synthetic peptides are mixed into the solution when the solution is at approximately 35° C.

\* \* \* \* \*